(12) United States Patent
Iwashita et al.

(10) Patent No.: US 9,826,735 B2
(45) Date of Patent: Nov. 28, 2017

(54) PERACETIC ACID TYPE STERILIZING COMPOSITION SOLUTION AND METHOD FOR STERILIZING CONTAINERS

(71) Applicant: TOYO SEIKAN GROUP HOLDINGS, LTD., Tokyo (JP)

(72) Inventors: Takeshi Iwashita, Yokohama (JP); Takaaki Harada, Yokohama (JP); Kenichi Kominami, Yokohama (JP)

(73) Assignee: TOYO SEIKAN GROUP HOLDINGS, LTD., Tokyo (JP)

( * ) Notice: Subject to any disclaimer, the term of this patent is extended or adjusted under 35 U.S.C. 154(b) by 323 days.

(21) Appl. No.: 14/417,942

(22) PCT Filed: May 1, 2013

(86) PCT No.: PCT/JP2013/062710
§ 371 (c)(1),
(2) Date: Jan. 28, 2015

(87) PCT Pub. No.: WO2014/020961
PCT Pub. Date: Feb. 6, 2014

(65) Prior Publication Data
US 2015/0208648 A1  Jul. 30, 2015

(30) Foreign Application Priority Data

Aug. 3, 2012 (JP) .................. 2012-172849

(51) Int. Cl.
| | |
|---|---|
| *A61L 2/18* | (2006.01) |
| *A01N 25/32* | (2006.01) |
| *A01N 37/02* | (2006.01) |
| *A01N 63/04* | (2006.01) |
| *A01N 37/16* | (2006.01) |
| *A01N 59/00* | (2006.01) |
| *B65B 55/10* | (2006.01) |

(52) U.S. Cl.
CPC ............ *A01N 25/32* (2013.01); *A01N 37/02* (2013.01); *A01N 37/16* (2013.01); *A01N 59/00* (2013.01); *A01N 63/04* (2013.01); *A61L 2/18* (2013.01); *A61L 2/186* (2013.01); *A61L 2202/23* (2013.01); *B65B 55/10* (2013.01)

(58) Field of Classification Search
CPC ..................................................... A61L 2/186
See application file for complete search history.

(56) References Cited

U.S. PATENT DOCUMENTS

2009/0269324 A1  10/2009  Herdt et al.
2009/0311134 A1  12/2009  Iwashita et al.

FOREIGN PATENT DOCUMENTS

| JP | 08-058744 A | 3/1996 |
|---|---|---|
| JP | 2008-279387 A | 11/2008 |
| JP | 2011-517946 A | 6/2011 |
| KR | 10-297165 B1 | 9/2002 |
| WO | 94/17833 A1 | 8/1994 |
| WO | 2007/148410 A1 | 12/2007 |
| WO | 2011/027288 A2 | 3/2011 |
| WO | 2011/107942 A2 | 9/2011 |

OTHER PUBLICATIONS

Communication dated Jan. 29, 2016 from the European Patent Office issued in corresponding Application No. 13825449.5.
International Search Report for PCT/JP2013/062710 dated Jul. 30, 2013 [PCT/ISA/210].

*Primary Examiner* — Sean E Conley
*Assistant Examiner* — Donald Spamer
(74) *Attorney, Agent, or Firm* — Sughrue Mion, PLLC

(57) ABSTRACT

A peracetic acid type sterilizing composition solution containing peracetic acid, acetic acid, hydrogen peroxide and catalase enzyme, wherein said sterilizing solution has a pH in a range of 2.6 to 5.0, said catalase enzyme is contained in an amount of 0.1 to 10 μg/ml, the concentration of said peracetic acid is 500 to 10,000 ppm, and the concentration of said hydrogen peroxide is less than 500 ppm. The concentration of the hydrogen peroxide can be efficiently decreased due to the catalase enzyme that is added in small amounts thereby suppressing the bubbling caused by the addition of the catalase enzyme.

7 Claims, No Drawings

US 9,826,735 B2

PERACETIC ACID TYPE STERILIZING COMPOSITION SOLUTION AND METHOD FOR STERILIZING CONTAINERS

CROSS REFERENCE TO RELATED APPLICATIONS

This application is a National Stage of International Application No. PCT/JP2013/062710 filed May 1, 2013, claiming priority based on Japanese Patent Application No. 2012-172849 filed Aug. 3, 2012, the contents of all of which are incorporated herein by reference in their entirety.

TECHNICAL FIELD

This invention relates to a peracetic acid type sterilizing composition solution containing a catalase enzyme that is used for sterilizing food containers. More specifically, the invention relates to a peracetic acid type sterilizing composition solution which suppresses bubbling caused by the catalase enzyme and efficiently expresses sterilizing power, and to a method for sterilizing containers using the same.

BACKGROUND ART

Peracetic acid type sterilizers have heretofore been used for sterilizing or pasteurizing food containers. In aseptically filling beverages, in particular, it is important that the containers, the contents and the filling environment are all made aseptic and, therefore, the peracetic type sterilizer has been used for sterilizing or pasteurizing the containers such as bottles and caps (patent document 1, etc.).

The peracetic acid type sterilizer comprises chiefly peracetic acid, acetic acid and hydrogen peroxide which are present in an equilibrium state. If the concentration of hydrogen peroxide is high, however, the hydrogen peroxide tends to stay in the container and it becomes necessary, after the sterilization, to wash the container with aseptic water to a sufficient degree. Further, it has been desired to suppress the concentration of the peracetic acid to be lower than the concentration that used to be employed in the customary methods.

To solve the above problem, there has been proposed a pasteurizing method using a sterilizing composition that comprises hydrogen peroxide, percarboxylic acid and carboxylic acid and that further contains 20 to 250 ppm of a catalase enzyme that is capable of decomposing the hydrogen peroxide (patent document 2).

According to the pasteurizing method that uses a sterilizing composition comprising hydrogen peroxide, percarboxylic acid and carboxylic acid and, further, containing the catalase enzyme, there is obtained such an advantage that the hydrogen peroxide is decomposed due to the catalase enzyme, the concentration of the hydrogen peroxide is lowered in the sterilizing composition, and efficient sterilization is realized maintaining stable sterilizing power for extended periods of time as a result of controlling the concentration of the hydrogen peroxide.

PRIOR ART DOCUMENTS

Patent Documents

Patent document 1: JP-A-8-58744
Patent document 2: JP-T-2011-517946

OUTLINE OF THE INVENTION

Problems that the Invention is to Solve

To decompose the hydrogen peroxide in the peracetic acid type sterilizing composition blended with the catalase enzyme, however, the catalase enzyme is necessary in such a relatively large amount as 20 to 250 ppm. Therefore, there newly occur such problems that bubbles evolve in large amounts when the hydrogen peroxide is decomposed and aggregates are formed due to the catalase enzyme. That is, if the concentration of the catalase enzyme is high, bubbles evolve due to the decomposition of the hydrogen peroxide and do not easily disappear since their surfaces are covered with a protein film and aggregates of protein are formed due to the catalase enzyme. Therefore, washing efficiency decreases in the step of washing with aseptic water that is conducted after the step of sterilization, and equipment is contaminated as the aggregates deposit on the storage tanks and the like. Moreover, nozzles are clogged with aggregates necessitating frequent cleaning operation and causing a decrease in the efficiency in the step of sterilization.

Besides, the catalase enzymatic preparation often contains inorganic salt such as sodium chloride that is contained in a culture medium for cultivating catalase-producing microorganisms. Further, when used as a catalase enzyme-containing solution, the catalase enzymatic preparation is often blended with a preservative for long-time storage maintaining stability and with sodium chloride or the like as a buffer agent, though the catalase enzymatic preparation does not have to be blended with them when it is used in the form of a powder or beads. If the peracetic acid type sterilizing composition solution obtained by simply adding the above catalase enzymatic preparation to the above peracetic acid type sterilizer is used, therefore, there occurs such a problem that pipes in the sterilizing apparatus are corroded due to chloride ions in the catalase enzymatic preparation.

It is, therefore, an object of the present invention to provide a peracetic acid type sterilizing composition solution containing the catalase enzyme that is capable of efficiently reducing the hydrogen peroxide despite the small amounts of catalase enzyme, capable of suppressing the bubbling and the formation of aggregates caused by the addition of the catalase enzyme, and capable of suppressing the concentration of the peracetic acid to be equal to, or lower than, that in the conventional methods, and to provide the method for preparing the same.

Another object of the present invention is to provide a method of sterilization capable of efficiently sterilizing the containers by using the peracetic acid type sterilizing composition solution that contains the catalase enzyme.

Means for Solving the Problems

According to the present invention, there is provided a peracetic acid type sterilizing composition solution containing peracetic acid, acetic acid, hydrogen peroxide and catalase enzyme, wherein the sterilizing solution has a pH in a range of 2.6 to 5.0, the catalase enzyme is contained in an amount of 0.1 to 10 µg/ml, the concentration of the peracetic acid is 500 to 10,000 ppm, and the concentration of the hydrogen peroxide is less than 500 ppm.

In the peracetic acid type sterilizing composition solution of the present invention, it is desired that:
1. The concentration of the chloride ions is not more than 10 µg/ml,
2. The chloride ions are stemming from the sodium chloride;
3. The catalase enzyme is stemming from the fungi; and 4. During the preparation of the sterilizing composition solution, the catalase enzyme is capable of decomposing not less than 35% of the hydrogen peroxide in less than 10 minutes.

According to the present invention, further, there is provided a method for preparing the peracetic acid type sterilizing composition solution by adjusting the pH of the peracetic acid type sterilizing solution that contains peracetic acid, acetic acid and hydrogen peroxide and, thereafter, adding the whole amount of the catalase enzyme thereto in a divided manner.

According to the present invention, there is further provided a method for sterilizing containers by adjusting the temperature of the peracetic acid type sterilizing composition solution to be 40 to 75° C. and applying the sterilizing composition solution to the surfaces of the containers.

Effects of the Invention

The peracetic acid type sterilizing composition solution of the present invention contains the catalase enzyme that is so highly active as to efficiently decompose the hydrogen peroxide, and has a pH that is adjusted to lie in a range of 2.6 to 5.0. Therefore, despite the content of the catalase enzyme is so small as 0.1 to 10 µg/ml, not less than 35% of the hydrogen peroxide can be decomposed in the sterilizing solution in less than 10 minutes. Therefore, the hydrogen peroxide in the sterilizing composition solution can be efficiently decomposed making it possible to maintain the concentration of the peracetic acid to be 500 to 10,000 ppm and the concentration of the hydrogen peroxide to be less than 500 ppm. The sterilizing composition solution, therefore, exhibits an excellent sterilizing power of a sterilizing level of not less than 5D as will become obvious from the results of Examples described later.

The bubbling and the formation of aggregates caused by the addition of the catalase enzyme can be suppressed without using any defoaming agent or the like. Therefore, no defoaming agent remains in the containers suppressing hygienic effect on the contents. Besides, the step of washing can be efficiently carried out for removing the sterilizing composition solution after the step of sterilization. Moreover, there is no such probability that the nozzles are clogged with aggregates, and the work for cleaning the bubbling and deposition needs be conducted very little frequency, making it possible to sterilize the containers efficiently and continuously facilitating the use of the sterilizing composition solution in a circulating manner since the sterilizing power is maintained stable.

Moreover, the catalase enzyme is used in small amounts and the peracetic acid type sterilizing composition solution maintains the sterilizing power stable for extended periods of time to also advantage in economy.

More than that, the concentration of the hydrogen peroxide is so low as less than 500 ppm. Therefore, no hydrogen peroxide remains on the surfaces of the containers despite the washing is conducted for only short periods of time, and the containers are maintained in excellently hygienic state after the sterilization.

Further, since the concentration of chloride ions has been adjusted to be not more than 10 µg/ml in the peracetic acid type sterilizing composition solution, there is no problem of causing corrosion to the pipes in the sterilizing apparatus.

MODES FOR CARRYING OUT THE INVENTION

The peracetic acid type sterilizer composition solution of the invention chiefly comprises peracetic acid, acetic acid and hydrogen peroxide, and is prepared by adding a pH-adjusting agent and a catalase enzyme to a peracetic acid type sterilizer in which the above components are present in an equilibrium state.

(Peracetic Acid Type Sterilizer)

There has heretofore been known a peracetic acid type sterilizer chiefly comprising peracetic acid, acetic acid and hydrogen peroxide which are present in an equilibrium state. The peracetic acid type sterilizing composition solution of the present invention can use the peracetic acid type sterilizer of various concentrations before being blended with the catalase enzyme. Desirably, however, the invention uses a peracetic acid type sterilizer comprising 10 to 25% by weight of peracetic acid, 20 to 40% by weight of acetic acid, 15 to 25% by weight of hydrogen peroxide, the rest of water and, as required, a stabilizer. As the peracetic acid type sterilizer, there can be used, for example, the Oxyper 100 (manufactured by Nihon Peroxide Co.: 10.2% by weight of peracetic acid, 20.6% by weight of acetic acid, 17.2% by weight of hydrogen peroxide) or the like, which is diluted with water to adjust the concentration.

(Catalase Enzyme)

The catalase enzyme has heretofore been known as an enzyme for decomposing the hydrogen peroxide. In the present invention, it is important that the catalase enzyme has resistance in the acidic region in the peracetic acid type sterilizer, and is the one comprising the catalase enzyme stemming from the fungi or comprising the catalase enzyme stemming from the bacteria. The invention preferably uses the catalase enzyme stemming from the fungi and, specifically, the catalase enzyme stemming from the *Aspergillus niger*. Only a single kind of catalase enzyme may be used or a plurality of kinds of catalase enzymes may be used being mixed together.

In the invention, there is no specific limitation on the form of the catalase enzyme that is used, and the catalase enzyme can be used in a variety of forms such as solution, powder, or being fixed in a water-insoluble substrate like beads. In the invention, it is desired to select a catalase enzyme that exhibits its activity over a pH range of 2.6 to 6.0. Then upon adjusting the pH of the peracetic acid type sterilizing composition solution to lie in a range of 2.6 to 5.0, not less than 35% of the hydrogen peroxide can be decomposed in less than 10 minutes by the addition of the catalase enzyme during the preparation of the sterilizing composition solution despite the amount of the catalase enzyme is as very small as 0.1 to 10 µg/ml.

As the catalase enzyme, though not limited thereto only, there can be used the catalase enzymatic preparations that are commercially available, such as Leonet F-35 and Leonet F Plus (manufactured by Nagase Chem-Tech Co.).

As described earlier, the catalase enzymatic preparation contains sodium chloride. To prevent the pipes from corroding, therefore, it is desired to use the catalase enzymatic preparation after the concentration of chloride ions therein has been decreased.

The salt can be removed from the catalase enzyme-containing solution relying on a conventional desalting method such as dialysis method, ultrafiltration method (ultrafiltration membrane, UF membrane treatment) or gel filtration method though not limited thereto only. It is, however, desired to remove the salt particularly by the ultrafiltration method from the standpoint of operability and productivity.

To maintain preservability of the catalase enzyme-containing solution, it is desired to add a specific preservative, to conduct the heat-sterilization treatment and/or the filtration treatment, or to conduct both of them after the desalting treatment in order to suppress or remove the proliferation of general bacteria or molds that could cause a decrease in the preservability.

It is important that the preservative that can be favorably used contains no salt, as a matter of course, has been authorized as a food additive, and is capable of suppressing the proliferation of general bacteria and molds without decreasing the activity of the catalase enzyme.

As such a preservative, though not limited thereto only, there can be exemplified sorbic acid type preservative, benzoic acid type preservative, paraoxybenzoic acid type preservative, propionic acid type preservative, dehydroacetic acid type preservative, spirit type preservative, and vitamin B1 type preservative. Among them, there can be preferably used sodium dehydroacetate, paraoxybenzoic acid ester, sodium benzoate and polylizine. It is desired to add at least one of them in an amount of 0.005 to 0.5% by weight relative to the catalase enzyme-containing solution.

The heat-sterilization treatment for improving preservability is desirably conducted by heating the catalase enzyme-containing solution at a temperature of 50 to 70° C. for 10 to 600 seconds after the desalting treatment. If the heating temperature is lower than the above range, the sterilization cannot be effected to a sufficient degree. If the heating temperature is higher than the above temperature, on the other hand, the activity of the catalase enzyme cannot be maintained.

It is important that the filtering treatment separates the bacteria that could cause a decrease in the preservability of the catalase enzyme-containing solution but does not separate the catalase enzyme. It is, therefore, desired to use a filtering device having a filter pore size in a range of 0.1 to 1.0 μm.

At least either the preservative may be added or the heat-sterilization treatment and/or the filtration treatment may be conducted. Upon executing both of them, however, the preservability can be further improved, which is desirable. If both the preservative is added and the heat-sterilization treatment and/or the filtration treatment are carried out, either of them may be conducted first. Desirably, however, the heat-sterilization treatment and/or the filtering treatment are conducted, first, bacteria that could decrease the preservability are removed and, thereafter, the preservative is added.

(pH-Adjusting Agent)

As described above, it is desired that the catalase enzyme used in the invention is so selected that it exhibits its activity over a pH range of 2.6 to 6.0. As for the peracetic acid type sterilizer, however, the peracetic acid undergoes the decomposition and its concentration decreases if the pH becomes not lower than 5.0, and the sterilizing power wanes.

In order for the catalase enzyme to most exhibit its action for decomposing the hydrogen peroxide, further, it is desired to so select the catalase enzyme that it exhibits its activity over a pH range of 3.0 to 6.0. In order for the peracetic acid to most exhibit its sterilizing effect, however, it is desired that the peracetic acid type sterilizer has a pH which is, specifically, not higher than 4.0.

From such a standpoint according to the present invention, it was discovered that upon maintaining the pH of the peracetic acid type sterilizing composition solution in a range of 2.6 to 5.0 and, specifically, 3.0 to 4.0, it is allowed to maintain the activity of the catalase enzyme without impairing the stability of the peracetic acid type sterilizer that serves as the sterilizer and to attain the action for decomposing the hydrogen peroxide to a sufficient degree despite the catalase enzyme is added in a small amount.

As the pH-adjusting agent for adjusting the pH of the peracetic acid type sterilizing composition solution to lie in the above range according to the present invention, there can be used a widely known alkaline composition such as sodium hydroxide and potassium hydroxide.

(Peracetic Acid Type Sterilizing Composition Solution)

The peracetic acid type sterilizing composition solution of the present invention is prepared by adding the pH-adjusting agent, water and catalase enzyme to the starting peracetic acid sterilizer in which peracetic acid, acetic acid and hydrogen peroxide are present in an equilibrium state.

As for the preparation, desirably, the pH-adjusting agent is added and mixed to the peracetic acid type sterilizer having a desired peracetic acid concentration based on a prerequisite that the concentration of the peracetic acid after diluted with water will lie in a range described below, the pH is adjusted to lie in a range of 2.6 to 5.0 and, thereafter, the catalase enzyme is so added that the concentration thereof is 0.1 to 10 μg/ml and, specifically, 0.1 to 3.0 μg/ml. The order of adding the pH-adjusting agent and the catalase enzyme is not necessarily limited as described above. Upon adding them in the above order, however, the activity of the catalase enzyme can be maintained to be a maximum.

The catalase enzyme may be added to the sterilizer in its whole amount at one time but, more preferably, is added thereto in its whole amount being divided into a plurality of times. This enables the hydrogen peroxide to be mildly decomposed with the catalase enzyme reliably suppressing the bubbling caused by the catalase enzyme.

With the peracetic acid type sterilizing composition solution of the invention, the catalase enzyme promotes the decomposition of the hydrogen peroxide, the concentration of the hydrogen peroxide is maintained to be less than 500 ppm throughout the step of preparing the sterilizing composition solution or of the sterilization, and the concentration of the peracetic acid is maintained in a range of 500 to 10,000 ppm and, specifically, 1,000 to 3,500 ppm to maintain excellent sterilizing power.

The peracetic acid type sterilizing composition solution of the invention, further, contains the acetic acid and, if the peractic acid remains in the above-mentioned range, the acetic acid remains in a range of 1,000 to 25,000 ppm.

Further, by using, as the catalase enzyme, a catalase enzymatic preparation of which the concentration of chloride ions has been decreased, pipes in the sterilizing apparatus can be prevented from corroding. In this case, it is desired that the amount of the chloride ions in the peracetic acid type sterilizing composition solution has been decreased to be not more than 10 μg/ml.

(Method for Sterilizing Containers)

In the method for sterilizing containers of the present invention, the above-mentioned peracetic acid type sterilizing composition solution is maintained at a temperature of 40 to 75° C. and, specifically, 50 to 65° C. and is applied to the surfaces of the containers. The containers will be a variety of known containers such as cans, bottles, plastic containers and the like.

That is, if the temperature of the peracetic acid type sterilizing composition solution is higher than the above range, decomposition of the peracetic acid is promoted, and proteins coagulate due to the catalase enzyme and choke the nozzle. Besides, among the known containers, the polyester bottles are adversely affected from the standpoint of resistance against the heat, too. If the temperature of the peracetic acid type sterilizing composition solution is lower than the above range, on the other hand, the sterilizing power decreases, an extended period of time is required for the sterilization, and the sterilizing efficiency decreases.

The peracetic acid type sterilizing composition solution of the invention can be applied onto the surfaces of the containers by a customary sterilizing method that uses the peracetic acid type sterilizer. Not being limited thereto only, however, it is also allowable to use a full-filling method in which the sterilizing composition solution is poured into the container from the upper side of the container that is in an upright state and, after the passage of a predetermined period of time, the container is turned into an inverted state and the sterilizing composition solution is drained, a straight flushing method in which the sterilizing composition solution is injected from the lower side of the container in an inverted state, directly hits the bottom inner surface of the container and flows down along the container wall, and a method in which the sterilizing composition solution mixed with the air is injected into the container from the lower side of the container in an inverted state.

In the present invention, the peracetic acid type sterilizing composition solution of the invention adjusted at the above temperature is brought into contact for 5 to 10 seconds to attain the sterilizing power of a sterilizing level of not less than 5D.

In the sterilizing method of the invention, the peracetic acid type sterilizing composition solution can be continuously used so far as the concentration of the peracetic acid is 500 to 10,000 ppm and the concentration of the hydrogen peroxide is less than 500 ppm. If the concentration of the hydrogen peroxide becomes not less than 500 ppm, then the catalase enzyme and, as required, the peracetic acid type sterilizer may be added to use the sterilizing composition solution in a circulating manner.

The containers sterilized by using the peracetic acid type sterilizing composition solution of the invention in the step of sterilization are washed with the aseptic water in the next step of washing to remove the peracetic acid type sterilizing composition solution that is remaining on the surfaces of the containers. The peracetic acid type sterilizing composition solution of this invention has a hydrogen peroxide concentration which is as low as less than 500 ppm. Therefore, despite of the washing for a short period of time, the hydrogen peroxide does not remain on the surfaces of the bottles, and the sterilized hygiene state is not lost.

EXAMPLES (Preparation of the Peracetic Acid Type Sterilizing Composition Solution)

The peracetic acid type sterilizing composition solution was prepared by using, as the peracetic acid type sterilizer, the Oxyper 100 (manufactured by Nihon Peroxide Co.: 10.2% by weight of peracetic acid, 20.6% by weight of acetic acid, 17.2% by weight of hydrogen peroxide), diluting it with water so that the concentrations of the peracetic acid were as shown in Tables 1 to 4, and adding a 5N aqueous solution of sodium hydroxide so that the pH was 2.0 to 5.5. Thereafter, the Leonet F Plus (manufactured by Nagase Chem-Tech Co., stemming from the *Aspergillus niger*) was added as the catalase enzyme in such an amount that the final concentration of the catalase enzyme was 0.1 to 10 μg/ml relative to the whole amount of the peracetic acid type sterilizing composition solution.

(Method for Measuring the Components of the Peracetic Acid Type Sterilizing Composition Solution)

1. Amount of the Peracetic Acid.

After the reaction with the catalase enzyme, the amount of the peracetic acid was measured by the potassium permanganate—iodine method. That is, the sample was titrated with the potassium permanganate under an acidic condition of sulfuric acid to measure the concentration of the hydrogen peroxide and was, thereafter, titrated with the sodium thiosulfate while adding the potassium iodide and a starch indicator thereto to measure the concentration of the peracetic acid.

As for the catalase enzyme reaction end time, measurement was taken for every 5 minutes after 5 minutes have passed from when the catalase enzyme was added to the peracetic acid type sterilizing composition solution, and the moment of when there was seen no reduction in the concentration of the hydrogen peroxide was regarded to be the end of the reaction, and the concentration at this moment was measured.

2. Amount of the Hydrogen Peroxide.

The amount of the hydrogen peroxide includes two concentrations, the one being a value of after the peracetic acid type sterilizer was diluted with water but before the catalase enzyme was added (value calculated from the concentration of the starting peracetic acid type sterilizer by taking the dilution into account) and the other being a value measured after the above-mentioned catalase enzyme reaction has been finished. The method of measurement complied with the method for measuring the amount of the peracetic acid described in 1. above.

3. Amount of the Catalase Enzyme.

The amounts of the catalase enzyme were measured according to the Experimental Protocol using the Nano Orange (registered trademark) Protein Quantitation Kit (manufactured by Invitrogen Co.) to be as shown in Tables 1 to 4.

(Method of Evaluation)

1. Power for Decomposing the Hydrogen Peroxide.

The peracetic acid type sterilizing composition solution was measured for its concentration of the hydrogen peroxide ($I_0$) just after the preparation thereof and for its concentration of the hydrogen peroxide (I) after 10 minutes have passed from the start of preparation, and from which a reduction ratio $[(I_0-I)/I_0] \times 100$ (%/10 min.) was calculated. The power for decomposing the hydrogen peroxide per 10 minutes was evaluated to be ○ if it was not less than 35% and X if it was less than 35%.

2. Peracetc Acid Decomposition Percentage.

The peracetic acid type sterilizing composition solution was measured for its concentration of the peracetic acid ($I_0$) just after the preparation thereof and for its concentration of the peracetic acid (I) after one hour has passed at 25° C. from the start of preparation, and from which a reduction ratio $[(I_0-I)/I_0] \times 100$ (%/hour) was calculated. The peracetic acid decomposition percentage per hour was evaluated to be ○ if it was not more than 1%, evaluated to be Δ if was 1 to 3%, and was evaluated to be X if it exceeded 3%.

3. Surface State of the Sterilizing Composition Solution in the Tank.

The surface of the peracetic acid type sterilizing composition solution was confirmed with the naked eye 5 minutes after the start of preparation of the peracetic acid type sterilizing composition solution. The surface was evaluated to be ○ if there was no bubbling or formation of aggregates and X if they were formed.

4. Effect for Sterilizing the Containers.

A 500 ml polyethylene terephthalate bottle (hereinafter referred to as bottle) was used as the container, and a bacteria solution was prepared by using *Bacillus cereus* ATCC 9139 as sample bacteria. The bacteria solution was uniformly blown from a sprayer onto the inner surface of the bottle such that the density thereof was $10^6$ cfu/bottle. Thereafter, the bottle was dried to obtain a bottle for evaluation. Next, the peracetic acid type sterilizing composition solution just after the catalase enzyme reaction has been finished was adjusted for its temperature to be 65° C., and was sprayed into the bottle for evaluation so as to be brought in contact therewith for 8 seconds. Next, the inner surface of the bottle was washed with the aseptic water. By using the standard agar culture medium, the aseptic water used for washing was measured for the number of living bacteria based on the membrane filter method. From the initial number of bacteria and the number of living bacteria, the sterilization effect (D) was found in compliance with the following formula. The testing was conducted a number of times n=3, and the sterilizing effect was evaluated with the average number of living bacteria as the number of living bacteria.

$D = LOG(N_0/N)$ wherein $N_0$ is the initial number of bacteria and N is the number of living bacteria.

If the D-value was not less than 6D, the sterilizing effect was high and was evaluated to be ○, if the D-value was not less than 5D but was less than 6D, the sterilizing effect was exhibited and was evaluated to be Δ and if the D-value was less than 5D, the sterilizing effect was low and was evaluated to be X.

Examples 1 to 3, Comparative Examples 1 and 2

The power for decomposing the hydrogen peroxide and the peracetic acid decomposition percentage were examined depending on the pH values. The peracetic acid type sterilizer was diluted such that the compositions were nearly the same except the pH value, i.e., such that the amount of the peracetic acid was about 3,000 to about 3,300 ppm and the initial amount of the hydrogen peroxide was about 4,500 to about 5,000 ppm. Thereafter, a 5N aqueous solution of sodium hydroxide was added thereto such that the pH values were as shown in Table 1, and the catalase enzyme was added thereto in an amount of 0.4 µg/ml to evaluate. The results were as shown in Table 1.

TABLE 1

| | Sterilizing composition solution | | | | | | Results of evaluation | | | |
|---|---|---|---|---|---|---|---|---|---|---|
| | | Amount of hydrogen peroxide | | | | | | Hydrogen | Peracetic acid | |
| | Amount of peracetic acid (ppm) | Before adding catalase (ppm) | After adding catalase (ppm) | | pH | Amount of catalase (µg/ml) | Method of adding catalase | peroxide decomposing power (%/10 min.) | decomposition percentage at 25° C. (%/hour) | |
| Ex. 1 | 3060 | 4682 | 136 | ○ | 2.6 | 0.4 | one time | 40 | ○ | 0 | ○ |
| Ex. 2 | 3154 | 4889 | 0 | ○ | 4.0 | 0.4 | one time | 88 | ○ | 0 | ○ |
| Ex. 3 | 3358 | 5373 | 0 | ○ | 5.0 | 0.4 | one time | 99 | ○ | 1 | Δ |
| Comp. Ex. 1 | 3094 | 4827 | 561 | X | 2.1 | 0.4 | one time | 28 | X | 0 | ○ |
| Comp. Ex. 2 | 3300 | 5214 | 0 | ○ | 5.5 | 0.4 | one time | 99 | ○ | 10 | X |

Examples 4 to 7, Comparative Examples 3 to 6

To compare the surface state of the sterilizing composition solution in the preparation tank and the power for decomposing the hydrogen peroxide depending on the amount of the catalase enzyme and on the blending method, the peracetic acid type sterilizer was diluted such the amount of the peracetic acid was about 3,000 to about 3,300 ppm and the initial amount of the hydrogen peroxide was about 4,500 to about 5,000 ppm, and the pH was adjusted to be 2.0 to 4.0. Thereafter, the catalase enzyme was added thereto in amounts of 0.12 to 20 µg/ml as shown in Table 2 to evaluate.

In Examples 4 to 6 and in Comparative Examples 3 to 6, the catalase enzyme was added at one time. In Example 7, however, the whole amount of the catalase enzyme was added in two times being divided into half just after the pH was adjusted and another half after 5 minutes have passed, and the concentrations of the peracetic acid and the hydrogen peroxide were measured just before the catalase enzyme was added in the second time (value marked with * in Table 2). In other respects, the evaluation was made in the same manner as in Example 4. The results were as shown in Table 2.

TABLE 2

| | Sterilizing composition solution | | | | | | Results of evaluation | | | |
|---|---|---|---|---|---|---|---|---|---|---|
| | | Amount of hydrogen peroxide | | | | | | Surface state of the sterilizing composition solution in the tank | | Hydrogen peroxide decomposing power |
| | Amount of peracetic acid (ppm) | Before adding catalase (ppm) | After adding catalase (ppm) | | pH | Amount of catalase (µg/ml) | Method of adding catalase | *1 | *2 | (%/10 min.) |
| Ex. 4 | 3116 | 5141 | 374 | ○ | 4.0 | 0.12 | one time | ○ | ○ | 65 | ○ |
| Ex. 5 | 3230 | 4684 | 0 | ○ | 4.0 | 1.2 | one time | ○ | ○ | 88 | ○ |
| Ex. 6 | 3353 | 4962 | 0 | ○ | 4.0 | 10 | one time | ○ | ○ | 100 | ○ |

TABLE 2-continued

| | Sterilizing composition solution | | | | | | Results of evaluation | | |
|---|---|---|---|---|---|---|---|---|---|
| | | Amount of hydrogen peroxide | | | | | Surface state of the sterilizing composition solution in the tank | | Hydrogen peroxide decomposing power |
| | Amount of peracetic acid | Before adding catalase | After adding catalase | pH | Amount of catalase | Method of adding catalase | | | |
| | (ppm) | (ppm) | (ppm) | | (μg/ml) | | *1 | *2 | (%/10 min.) |
| Comp. Ex. 3 | 3326 | 5122 | 1224 | X 4.0 | 0.04 | one time | ○ | ○ | 34 X |
| Comp. Ex. 4 | 3298 | 4947 | 0 | ○ 4.0 | 15 | one time | X | ○ | 100 ○ |
| Comp. Ex. 5 | 3281 | 5053 | 0 | ○ 4.0 | 20 | one time | X | X | 100 ○ |
| Comp. Ex. 6 | 3000 | 4590 | 0 | ○ 2.0 | 20 | one time | X | X | 100 ○ |
| Ex. 7 | 3362 | 5043 | 0* | ○ 4.0 | 0.48 | *3 | ○ | ○ | 100 ○ |

*1: Bubbling
*2: Aggregates
*3: divided into 2 times

Examples 8 to 11, Comparative Examples 7 and 8

How the effect for sterilizing the containers would be affected was examined depending on the amount of the peracetic acid and the amount of the hydrogen peroxide. As shown in Table 3, the peracetic acid type sterilizer was diluted such the amount of the peracetic acid was about 300 to about 15,000 ppm and the initial amount of the hydrogen peroxide was about 400 to about 24,000 ppm, and the pH was adjusted to be 4.0. Thereafter, the catalase enzyme was added thereto in amounts of 0.4 to 10 μg/ml as shown in Table 3 to evaluate.

As described above, since the amount of the catalase enzyme has been varied, the surface states of the sterilizing composition solutions in the preparation tanks were also evaluated. The results were as shown in Table 3.

Examples 12 and 13, Comparative Example 9

How the effect for sterilizing the containers would be affected was confirmed depending on the concentration of the hydrogen peroxide in the peracetic acid type sterilizing composition solution in which the amount of the peracetic acid was in a low-concentration region. As shown in Table 4, the peracetic acid type sterilizer was diluted such the amount of the peracetic acid was about 1,000 ppm and the initial amount of the hydrogen peroxide was about 1,600 ppm, and the pH was adjusted to be 4.0. Thereafter, the catalase enzyme was added thereto in amounts of 0.4 μg/ml to decrease the amount of the hydrogen peroxide to 0 ppm. The sterilizing composition solution was then heated at 85° C. for 5 minutes to deactivate the catalase enzyme and to which the hydrogen peroxide as added to be about 200 to about 700 ppm as shown in Table 4 to evaluate. The results were as shown in Table 4.

TABLE 3

| | Sterilizing composition solution | | | | | | | Results of evaluation | | |
|---|---|---|---|---|---|---|---|---|---|---|
| | | Amount of hydrogen peroxide | | | | | | | Surface state of the sterilizing composition solution in the tank | |
| | Amount of peracetic acid | Before adding catalase | After adding catalase | pH | Amount of catalase | Method of adding catalase | Effect for sterilizing containers | | | |
| | (ppm) | (ppm) | (ppm) | | (μg/ml) | | | *1 | *2 | |
| Ex. 8 | 527 | 812 | 0 ○ | 4.0 | 0.4 | one time | Δ | ○ | ○ | |
| Ex. 9 | 1105 | 1790 | 0 ○ | 4.0 | 0.4 | one time | ○ | ○ | ○ | |
| Ex. 10 | 5270 | 8327 | 0 ○ | 4.0 | 1 | one time | ○ | ○ | ○ | |
| Ex. 11 | 9880 | 14919 | 0 ○ | 4.0 | 2.5 | one time | ○ | ○ | ○ | |
| Comp. Ex. 7 | 289 | 448 | 0 ○ | 4.0 | 0.4 | one time | X | ○ | ○ | |
| Comp. Ex. 8 | 15810 | 24347 | 986 X | 4.0 | 10 | one time | ○ | X | X | |

*1: Bubbling
*2: Aggregates

TABLE 4

| | Sterilizing composition solution | | | | | | Results of evaluation Effect for sterilizing containers |
|---|---|---|---|---|---|---|---|
| | Amount of peracetic acid (ppm) | Amount of hydrogen peroxide | | pH | Amount of catalase (µg/ml) | Method of adding catalase | |
| | | Before adding catalase (ppm) | After adding catalase (ppm) | | | | |
| Ex. 12 | 1064 | 1628 | 235 ○ | 4.0 | 0.4 | one time | ○ |
| Ex. 13 | 1064 | 1628 | 480 ○ | 4.0 | 0.4 | one time | Δ |
| Comp. Ex. 9 | 1064 | 1628 | 682 X | 4.0 | 0.4 | one time | X |

Examples 14 to 17, Comparative Examples 10 and 11

The effect upon the sterilizing pipelines was examined depending on the difference in the concentration of the chloride ions in the peracetic acid type sterilizing composition solution.

The peracetic acid type sterilizer was diluted such that the compositions were nearly the same except the concentration of the chloride ions in the peracetic acid type sterilizing composition solution, i.e., such that the amount of the peracetic acid was 3,000 ppm and the initial amount of the hydrogen peroxide was 4,800 ppm. Thereafter, the pH was adjusted to be 4.0. To the above peracetic acid type sterilizing composition solution was added a catalase enzyme-containing solution that has been desalted by using a UF membrane (manufactured by Asahi Kasei Co.: Microza UF Module, ACV-3010) so that the concentration of the catalase enzyme was 0.4 µm/ml to decrease the amount of the hydrogen peroxide to 0 ppm. Next, the sodium chloride was so added that the concentration of the chloride ions in the peracetic acid type sterilizing composition solution was 0 to 20 µm/ml to thereby obtain an initial peracetic acid type sterilizing composition solution for evaluation.

The concentrations of the chloride ions were measured as described below. Table 5 shows the concentrations of the chloride ions in the peracetic acid type sterilizing composition solutions.

(Measuring the Concentrations of the Chloride Ions)

Concentrations of the chloride ions were measured by using the Ion Chromatograph, DX-320, manufactured by DIONEX Co. under the following conditions.
  Column: AS11-HC (4×250 mm)
  Guard Column: AG11-HC (4×50 mm)
  Temperature: 35° C.
  Eluent: KOH aqueous solution (gradient)
    0-8 min. (1 mmol/L)
    8-10 min. (1-7 mmol/L)
    10-19 min. (7-14 mmol/L)
    19-23 min. (14-23 mmol/L)
    23-28 min. (23-45 mmol/L)
    28-35 min. (45 mmol/L)
  Flow rate: 1.1 mL/min.
  Amount of injection: 25 µL
  Detector: Electrical conductivity detector (using suppressor)
  Suppressor: External mode, 170 mA An SUS stainless steel pipe (4 cm in diameter and 10 cm in length) used as a sterilizer pipeline was dipped in the peracetic acid type sterilizing composition solution, was stored at 40° C. for 6 months, and was evaluated. The amount of the peracetic acid varies with the passage of time. Therefore, the peracetic acid type sterilizing composition solution was replaced by the new one at a moment when the amount of the peracetic acid decreased down to 2800 ppm or less to maintain the amount of the peracetic acid to be 2800 to 3000 ppm.

The inner and outer surfaces of the stainless steel pipe were observed with the naked eye, and were evaluated to be ○ if there was no corrosion such as rust or pitting, evaluated to be Δ if they were discolored though there was no corrosion such as rust or pitting, and evaluated to be X if they were corroded. The results were as shown in Table 5.

TABLE 5

| | | Concentration of chloride ions (µg/ml) | Corrosion |
|---|---|---|---|
| Example | 14 | 0 | ○ |
| | 15 | 1 | ○ |
| | 16 | 5 | ○ |
| | 17 | 10 | Δ |
| Comp. Ex. | 10 | 12 | X |
| | 11 | 20 | X |

INDUSTRIAL APPLICABILITY

The peracetic acid type sterilizer composition solution of the invention is capable of efficiently decomposing the hydrogen peroxide in the sterilizing composition solution despite the content of the catalase enzyme is as very small as 0.1 to 10 µg/ml. Therefore, the peracetic acid type sterilizer composition solution of the invention is excellent in economy, can suppress the formation of bubbling or aggregates caused by the addition of the catalase enzyme, eliminates the need of frequency cleaning the tanks and the sterilizing injectors enabling the sterilization to be efficiency carried out and, therefore, can also be effectively used for the method for sterilizing the products in large quantity.

Moreover, the concentration of the hydrogen peroxide has been decreased down to be less than 500 ppm and no defoaming agent has been used, either. Therefore, the hydrogen peroxide does not remain despite the washing is conducted for only a short period of time after the sterilization, suppressing the hygienic effect on the contents.

By using the catalase enzymatic preparation having a decreased concentration of the chloride ions, further, it is made possible to suppress the pipes from corroding providing usefulness specifically for the method for sterilizing the products in large quantity.

The invention claimed is:

1. A sterilizing composition solution containing peracetic acid, acetic acid, hydrogen peroxide and catalase enzyme, wherein said sterilizing solution has a pH in a range of 3.0 to 5.0, said catalase enzyme is contained in an amount of 0.1 to 10 µg/ml, a concentration of said peracetic acid is 500 to 10,000 ppm, and a concentration of said hydrogen peroxide is less than 500 ppm.

2. The sterilizing composition solution according to claim 1, wherein a concentration of chloride ions is not more than 10 µg/ml.

3. The sterilizing composition solution according to claim 2, wherein said chloride ions are stemming from sodium chloride.

4. The sterilizing composition solution according to claim 1, wherein said catalase enzyme is stemming from fungi.

5. The sterilizing composition solution according to claim 1, wherein during the preparation said sterilizing composition. solution, said catalase enzyme is capable of decomposing not less than 35% of said hydrogen peroxide in less than 10 minutes.

6. A method for preparing the sterilizing composition solution of claim 1 by adjusting the pH of the sterilizing solution that contains peracetic acid, acetic acid and hydrogen peroxide and, thereafter, adding the whole amount of the catalase enzyme thereto in a divided manner.

7. A method for sterilizing containers by adjusting the temperature of the sterilizing composition solution of claim 1 to be 40 to 75° C. and applying said sterilizing composition solution to surfaces of the containers.

* * * * *